(12) United States Patent
Hupperts et al.

(10) Patent No.: US 6,399,807 B1
(45) Date of Patent: Jun. 4, 2002

(54) METHOD FOR PRODUCTION OF 2,4,5-TRIFLUORO-BENZONITRILE

(75) Inventors: Achim Hupperts, Düsseldorf; Reinhard Lantzsch, Wuppertal, both of (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/446,491

(22) PCT Filed: Jun. 18, 1998

(86) PCT No.: PCT/EP98/03732

§ 371 (c)(1), (2), (4) Date: Dec. 21, 1999

(87) PCT Pub. No.: WO99/01425

PCT Pub. Date: Jan. 14, 1999

(30) Foreign Application Priority Data

Jul. 1, 1997 (DE) ......................... 197 27 890

(51) Int. Cl.$^7$ ............................. C07C 253/30
(52) U.S. Cl. ..................................... 558/350
(58) Field of Search ......................... 558/350

(56) References Cited

U.S. PATENT DOCUMENTS

| | | | | |
|---|---|---|---|---|
| 2,044,015 | A | * 6/1936 | Perkins et al. | 558/350 |
| 5,110,026 | A | 5/1992 | Messner | 226/152 |
| 5,416,235 | A | * 5/1995 | Gilbert et al. | 558/350 |
| 5,496,793 | A | 3/1996 | Andree et al. | 504/273 |
| 5,565,612 | A | * 10/1996 | Pfirmann et al. | 564/442 |

FOREIGN PATENT DOCUMENTS

| | | |
|---|---|---|
| CA | 2090768 | 8/1993 |
| CA | 2102750 | 5/1994 |
| CA | 2119673 | 9/1994 |
| EP | 0 191 185 A | 8/1986 |
| EP | 0 415 585 | 3/1991 |
| EP | 0 433 124 | 6/1991 |
| EP | 0 497 239 | 8/1992 |
| EP | 0 566 268 | 10/1993 |
| EP | 0 682 008 A | 11/1995 |
| EP | 0 635 486 | 12/1998 |
| FR | 2 632 648 A | 12/1989 |
| GB | 951770 | 3/1964 |
| GB | 1 131 501 A | 10/1968 |

OTHER PUBLICATIONS

J. Med. Chem. (month unavailable) 1988, vol. 31, pp. 983–991, Sanchez et al, Quinolone Antibacterial Agents. Synthesis and Structure–Activity Relationships of 8–Substituted Quinoline–3–carboxylic Acids and 1,8–Naphthyridine–3–carboxylic Acids.

Coll. Czech. Chem. Com., vol. 42, (month unavailable) 1977, Cervená et al, Fluorinated Tri–cyclic Neuroleptics: 6,7–Difluoro Derivative of Chlorprothixene and 2–Fluoro–3–Hydroxy Derivative of Octoclothepin, pp. 2001–2017.

"Houben–Weyl Methoden der Organischen Chemie, 4. Auflage, Band X/3, Teil 3" 1965, Georg Thieme Verlag, Stuttgart, DE XP002081804, see p. 30–p. 31.

* cited by examiner

*Primary Examiner*—Laura L. Stockton
(74) *Attorney, Agent, or Firm*—Joseph C. Gil; James R. Franks

(57) ABSTRACT

The invention relates to a process for preparing 2,4,5-trifluoro-benzonitrile of the formula (I)

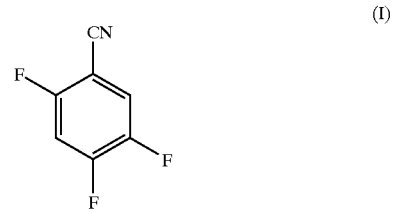

in which 2,4,5-trifluoro-aniline of the formula (II)

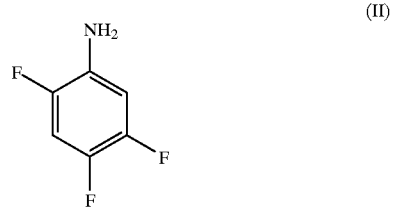

is, in a first step A), reacted with a nitrosating agent in the presence of a diluent and in which, in a second step B), the reaction product obtained in step A) is reacted with an alkali metal cyanide in the presence of a transition metal compound, an acid acceptor and a diluent.

13 Claims, No Drawings

METHOD FOR PRODUCTION OF 2,4,5-TRIFLUORO-BENZONITRILE

This application is a 371 of PCT/EP98/03732 filed Jun. 18, 1998.

TECHNICAL FIELD OF THE INVENTION

The invention relates to a process for preparing 2,4,5-trifluoro-benzonitrile which is used as starting material for active compounds in the fields of medicine and agriculture.

BACKGROUND OF THE INVENTION

It is known that 2,4,5-trifluoro-benzonitrile is obtained when 1-bromo-2,4,5-trifluorobenzene is heated with copper (I) cyanide and N-methyl-pyrrolidone in a closed reaction vessel at temperatures between 170° C. and 190° C. for several hours (see EP-A-191 185). However, this synthesis process affords a highly contaminated product which can be isolated in a satisfactory purity only after column chromatography.

According to a somewhat modified process, 1-bromo-2,4,5-trifluoro-benzene can also be converted with copper(I) cyanide into 2,4,5-trifluoro-benzonitrile using N,N-dimethyl-formamide as solvent and prolonged heating under reflux (see J. Med. Chem. 31 (1988), 983–991). However, this application does not describe the isolation of pure 2,4,5-trifluoro-benzonitrile.

Also known is the reaction of 2,4-dichloro-5-fluoro-benzonitrile with potassium fluoride, if appropriate in the presence of reaction auxiliaries, such as, for example, caesium fluoride and octadecyl-trimethylammonium chloride, in the presence of diluents, such as, for example, dimethyl sulphoxide, tetramethylene sulphone (sulpholane) and toluene, at temperatures above 150° C. (see EP-A-431 373, EP-A-433 124, EP-A-497 239, EP-A-635 486). However, here 2,4,5-trifluoro-benzonitrile is in most cases obtained in addition to other products, and only in low or moderate yields. Only if relatively large amounts of phase-transfer catalysts, in particular tetraalkylphosphonium halides, are employed, 2,4,5-trifluoro-benzonitrile is said to be obtained in relatively high yields (see EP-A-557 949).

It is furthermore known that 2,4,5-trifluoro-benzonitrile can be obtained in a mixture with other fluorination products by reaction of 2,4-difluoro-benzonitrile with elemental fluorine at low temperatures (see EP-A-566 268).

The synthesis of some trihalogenobenzonitriles—however, not that of 2,4,5-trifluoro-benzonitrile—has also been described starting from the corresponding trihalogenoanilines via the diazonium salts and their reaction with metal cyanides (for this "Sandmeyer process", see GB-A-951 770, Coll. Czech. Chem. Com. 42 (1977), 2001–2017). However, quality and/or yield of the resulting products are unsatisfactory.

DETAILED DESCRIPTION OF THE INVENTION

It is an object of the present invention to provide a process which permits the preparation of 2,4,5-trifluoro-benzonitrile in high purity and large yields starting from 2,4,5-trifluoro-aniline.

This object is achieved by a process for preparing 2,4,5-trifluoro-benzonitrile of the formula (I)

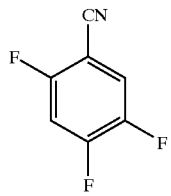

in which 2,4,5-trifluoro-aniline of the formula (II)

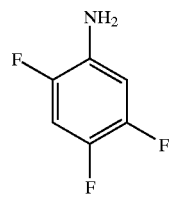

is, in a first step A), reacted with a nitrosating agent in the presence of a diluent and in which, in a second step B), the reaction product obtained in step A) is reacted with an alkali metal cyanide in the presence of a transition metal compound, an acid acceptor and a diluent.

Surprisingly, 2,4,5-trifluoro-benzonitrile can be obtained by the process according to the invention in a large yield and in high purity.

When carrying out the process according to the invention, the reaction temperatures can be varied within a relatively wide range. In general, the first step is carried out at temperatures between −20° C. and +30° C., preferably between −10° C and +20° C., and the second step is generally carried out at temperatures between −10° C. and +40° C., preferably between 0° C. and +30° C.

The two steps of the process according to the invention are generally carried out under atmospheric pressure. However, it is also possible to carry out the process according to the invention under elevated or reduced pressure—generally between 0.1 bar and 10 bar.

The starting material 2,4,5-trifluoro-aniline is known and can be prepared in a simple manner (see GB-A-11 31 501, EP-A-415 585).

The first step of the process according to the invention is carried out using a nitrosating agent. Suitable nitrosating agents are the nitrosating agents which are conventionally used for preparing diazonium salts. Examples of these are: Alkali metal nitrites, such as, for example, sodium nitrite and potassium nitrite (in the presence of an acid, such as, for example, sulphuric acid, methanesulphonic acid, formic acid or acetic acid), alkyl nitrites, such as, for example, methyl, ethyl, n- or i-propyl, n-, i-, s- or t-butyl, n-, i-, s- or t-pentyl nitrite, and furthermore also nitrosylsulphuric acid.

A particularly preferred nitrosating agent for carrying out the first step of the process according to the invention is nitrosylsulphuric acid.

The second step of the process according to the invention is carried out using an alkali metal cyanide. Preferred alkali metal cyanides are sodium cyanide or potassium cyanide. In addition, a transition metal compound, preferably a copper compound, such as, for example, copper cyanide or copper sulphate is used. Surprisingly, the transition metal compound can be employed in amounts which are far below the stoichiometric amount, i.e. in catalytic amounts.

The second step of the process according to the invention is furthermore carried out in the presence of an acid acceptor. Suitable acid acceptors are, in general, the customary inorganic or organic bases or acid binders. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiisopropylamine, N,N-dimethylcyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

Preference is given to using alkali metal carbonates or bicarbonates or alkaline earth metal carbonates or bicarbonates, such as, for example, sodium (bi)carbonate or potassium (bi)carbonate.

The process according to the invention is carried out in the presence of a diluent. Suitable diluents for carrying out the process according to the invention are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; carboxylic acid, such as, for example, formic acid, acetic acid or propionic acid; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

Particularly preferred diluents for carrying out the first step of the process according to the invention are carboxylic acids. When carrying out the second step of the process according to the invention, preference is given to using water as additional solvent.

For carrying out the first step of the process according to the invention, generally between 0.9 and 1.2 mol, preferably between 1.0 and 1.1 mol of a nitrosating agent are employed per mole of 2,4,5-trifluoro-aniline of the formula (II).

In a preferred embodiment of the first step of the process according to the invention, the 2,4,5-trifluoro-aniline of the formula (II) is initially charged in a suitable diluent, and the nitrosating agent is slowly metered in with stirring. The reaction mixture is then stirred until the reaction according to the first step has virtually ended.

For carrying out the second step of the process according to the invention, generally between 1 and 10 mol, preferably between 2 and 8 mol, of an alkali metal cyanide and generally between 0.01 and 0.5 mol, preferably between 0.05 and 0.2 mol, of a transition metal compound are employed per mole of the 2,4,5-trifluoro-aniline of the formula (II) employed in step 1.

In a preferred embodiment of the second step of the process according to the invention, the reaction mixture obtained according to the first step is added with stirring to an aqueous solution of alkali metal cyanide and transition metal compound, and the pH is maintained more or less in the neutral range by simultaneous addition of an acid acceptor. The reaction mixture is then stirred until the reaction has virtually ended.

The reaction product obtained in the first step is preferably not isolated prior to the reaction in the second step.

Work-up and isolation of the reaction product of the formula (I) can be carried out in a customary manner. The reaction mixture is, for example, shaken with an organic solvent which is virtually immiscible with water, such as, for example, ethyl acetate, and the solvent is then carefully distilled off under reduced pressure from the organic extraction solution, leaving the product of the formula (I) as residue.

The compound 2,4,5-trifluoro-benzonitrile of the formula (I) preparable by the process according to the invention can be used as intermediate for preparing active compounds in the fields of medicine and agriculture (see EP-A-191 185, EP-A-597 360, EP-A-617 026, EP-A-654 468).

PREPARATION EXAMPLES

EXAMPLE 1

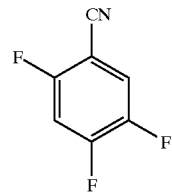

4.4 g (30 mmol) of 2,4,5-trifluoro-aniline are dissolved in 25 ml of acetic acid ("glacial acetic acid") and cooled using an ice-bath. With stirring, 4.5 g (31.5 mmol) of nitrosylsulphuric acid are then added, the ice-bath is removed and the reaction mixture is stirred for an additional hour (first step).

With stirring, the resulting diazonium salt solution is then added to a solution, cooled to 5° C., of 7.8 g (160 mmol) of sodium cyanide and 0.3 g (3 mmol) of copper(I) cyanide in 40 ml of water. By simultaneous addition of approximately 80 ml of a 25% strength aqueous solution of sodium carbonate, the pH is maintained approximately in the neutral range. The reaction mixture is subsequently stirred for approximately another 15 minutes and then extracted twice with 100 ml of ethyl acetate each time. The solvent is carefully distilled off under water pump vacuum from the combined organic extraction solutions.

This gives 4.1 g (92% pure product according to gas chromatographic analysis, i.e. 80% of theory) of 2,4,5-trifluoro-benzonitrile as an oily residue.

What is claimed is:

1. A process for preparing 2,4,5-trifluoro-benzonitrile, comprising:

a) reacting 2,4,5-trifluoro-aniline with a nitrosating agent in the presence of a diluent;

b) adding the product obtained in step a) to an aqueous solution of an alkali metal cyanide and a transition metal compound, said transition metal compound being present in said aqueous solution in a catalytic amount of from 0.01 mole to 0.5 mole per mole of the 2,4,5-trifluoro-aniline of step a); and c) adding to said aqueous solution concurrently with step b) an acid acceptor, such that the pH of said aqueous solution is maintained in the neutral range.

2. The process of claim 1, wherein the reaction in step a) is carried out at a temperature between −20° C. and +30° C., and the reaction in concurrent steps b) and c) is carried out at a temperature between −10° C. and +40° C.

3. The process of claim 1 wherein the nitrosating agent is selected from a group consisting of an alkali metal nitrite, an alkyl nitrite and a nitrosylsulphuric acid.

4. The process of claim 3 wherein the nitrosating agent is nitrosylsulphuric acid.

5. The process of claim 1 wherein the alkali metal cyanide is selected from the group consisting of sodium cyanide and potassium cyanide.

6. The process of claim 1 wherein the transition metal compound is a copper compound.

7. The process of claim 1 wherein the acid acceptor is selected from the group consisting of an alkali metal carbonate, an alkaline earth metal carbonate, an alkali metal bicarbonate and an alkaline earth metal bicarbonate.

8. The process of claim 1 wherein the diluent in step a) comprises one or more inert organic solvents.

9. The process of claim 8, wherein the diluent in step a) is a carboxylic acid.

10. The process of claim 1 wherein the product obtained in step a) is not isolated prior to the reaction in concurrent steps b) and c).

11. The process of claim 1 wherein the reaction in step a) is carried out at a temperature of between −10° C. and +20° C., and the reaction in concurrent steps b) and c is carried out at a temperature of between 0° C. and +30° C.

12. The process of claim 6 wherein the copper compound is selected from the group consisting of copper cyanide and copper sulfate.

13. The process of claim 1 wherein said transition metal compound is present in said aqueous solution of step b) in an amount of from 0.05 mole to 0.2 mole per mole of the 2,4,5-trifluoro-aniline of step a).

* * * * *